United States Patent [19]

Faasse, Jr.

[11] Patent Number: 5,402,780
[45] Date of Patent: Apr. 4, 1995

[54] MEDICAL ELECTRODE WITH OFFSET CONTACT STUD

[76] Inventor: Adrian L. Faasse, Jr., 10499 Braska Dr., Middleville, Mich. 49333

[21] Appl. No.: 115,864

[22] Filed: Sep. 2, 1993

[51] Int. Cl.⁶ .......................... A61B 5/04; A61N 1/04
[52] U.S. Cl. .................... 128/641; 607/149; 607/152; 29/877
[58] Field of Search ............... 128/640, 641; 607/149, 607/152, 153; 29/825, 876, 877

[56] References Cited

U.S. PATENT DOCUMENTS

| | | | |
|---|---|---|---|
| 3,845,757 | 11/1974 | Weyer | 128/641 |
| 3,977,392 | 8/1976 | Manley | |
| 4,166,453 | 9/1979 | McClelland | |
| 4,166,465 | 7/1985 | Esty et al. | |
| 4,270,543 | 6/1981 | Tabuchi et al. | |
| 4,304,235 | 12/1981 | Kaufman | |
| 4,350,165 | 9/1982 | Striese | |
| 4,370,984 | 2/1983 | Cartmell | 128/640 |
| 4,522,211 | 6/1985 | Bare et al. | 128/640 |
| 4,559,950 | 12/1985 | Vaughan et al. | |
| 4,633,879 | 1/1987 | Ong | |
| 4,640,289 | 2/1987 | Craighead | |
| 4,643,193 | 2/1987 | DeMarzo | |
| 4,763,659 | 8/1988 | Dunseath, Jr. | |
| 4,773,424 | 9/1988 | Inoue et al. | |
| 4,798,208 | 1/1989 | Faasse, Jr. | |
| 4,846,185 | 7/1989 | Carim | |
| 4,848,353 | 7/1989 | Engel | 128/640 |
| 4,865,039 | 9/1989 | Dunseath, Jr. | |
| 4,926,878 | 5/1990 | Snedeker | |
| 4,934,383 | 6/1990 | Glumac | 607/152 |
| 4,974,594 | 12/1990 | Berlin | |
| 4,979,517 | 12/1990 | Grossman et al. | |
| 5,003,978 | 4/1991 | Dunseath, Jr. | |
| 5,125,405 | 6/1992 | Schmid | |
| 5,150,708 | 9/1992 | Brooks | |

*Primary Examiner*—Lee S. Cohen
*Attorney, Agent, or Firm*—Price, Heneveld, Cooper, DeWitt & Litton

[57] ABSTRACT

The specification discloses a medical electrode particularly well suited for use as a diagnostic or monitoring electrode wherein conductive elements comprising a gel layer and a conductive bridge are intimately mounted on the adhesive top surface of a carrier layer, which includes an opening of dimensions similar to but smaller than the gel layer. A top layer, of at least equal surface area, is also affixed to the adhesive top surface of the carrier layer, sandwiching the indicated conductive elements between the top layer and the carrier layer such that the gel layer is exposed to a patient's skin but cannot be removed from the electrode. An electrically conductive contact means is provided to connect the conductive bridge to the desired monitoring/diagnostic apparatus. The carrier layer also includes an adhesively coated undersurface, which attaches to a patient's skin.

28 Claims, 1 Drawing Sheet

MEDICAL ELECTRODE WITH OFFSET CONTACT STUD

BACKGROUND OF THE INVENTION

The present invention relates to disposable, medical electrodes. Medical electrodes are adhered to a patient's body either to collect or introduce electricity at specific points. Those electrodes collecting electricity are categorized as either monitoring or diagnostic electrodes. The so-called "TENS electrodes" are categorized among those electrodes which introduce electricity into the patient's body. The present invention is particularly useful for monitoring/diagnosing a patient's physiological potentials, as in an electrocardiogram examination. However, it can also be adapted for use as a TENS electrode.

The principal functional components of the typical prior art monitoring/diagnostic electrode include a conductive layer, a conductive contact to which leads from a monitoring/diagnostic apparatus can be connected, and a support member upon which the two aforementioned components are mounted. Generally, the support or carrier has a conductive-adhesive backing so that the electrode can be securely fastened to the patient. The conductive layer and contact are typically a conductive hydrogel and a metal snap fastener, respectively. In some of the prior art, U.S. Pat. No. 3,977,392 being exemplary, the conductive hydrogel and metal snap fastener are spaced apart on the carrier medium. A strip of conductive material, such as silver foil, acts as a bridge between the two components to complete the electrical connection. Such a configuration is known as an offset electrode. Offset electrodes are known in the prior art to be advantageous over electrodes which intimately connect the snap fastener to the hydrogel, since the latter configuration speeds up corrosion of the snap fastener. This corrosion jeopardizes the accuracy of the electrode, making it all but useless.

Under either the offset or direct-connect configurations, the prior art discloses a variety of methods for attaching all the necessary conductive components to the carrier or support. U.S. Pat. No. 3,977,392 discloses essentially disc-shaped conductive hydrogel, resting in an opening in the carrier of approximately the same size as the hydrogel. The conductive layer of silver foil, being slightly less wide than the hydrogel disc, is placed on top of the carrier, conductively connecting the hydrogel and a metallic snap-fastener stud. A top layer, having an adhesive underside, is placed on the carrier medium, trapping the conductive components underneath. The adhesive underside of this top layer adheres to those portions of the hydrogel not covered by the conductive foil. Thus, the hydrogel is maintained in its opening in the carrier medium. However, in practice this method is not always effective. Being "sticky" by nature, the hydrogel will often adhere to the release paper or other protective backing, overcoming the adhesive effects of the aforementioned top layer. This has the effect of pulling the hydrogel from the carrier medium, such that the user is forced to tamper with the gel to get it back in place or abandon the electrode and try again.

U.S. Pat. No. 4,559,950 discloses an alternative arrangement where a silver-ink coated conductive layer directly contacts a patient's skin. The conductive hydrogel is maintained in a reservoir on top of the conductive layer. When pressure is applied to the reservoir, the hydrogel moves through a narrow slot in the conductive layer to form a more sensitive bridge between the patient's skin and the conductive layer. The ring-shaped reservoir of '950 has an adhesive underside, by which it is attached to the considerably smaller conductive layer, leaving additional areas of adhesive to attach the entire electrode to a patient's skin.

Still other medical electrodes either employ no hydrogel per se or use an adhesive conductive gel which is simply "stuck" to the surface of the conductive bridge in an offset-type electrode. For those monitoring/diagnostic electrodes which employ no conductive hydrogel, the accuracy of their electrical signal transmission can be seriously jeopardized where a patient's skin is covered with a substantial amount of hair fibers. Neither does merely attaching, as in the alternative configuration, an adhesive hydrogel to the surface of the conductive bridge insure that the gel will adhere to the electrode where the unit is misplaced on a patient's body and must be removed and repositioned.

SUMMARY OF THE INVENTION

In the medical electrode of the present invention, the carrier layer is adhesively coated at least on its bottom surface, and includes an opening of slightly smaller dimensions than the hydrogel layer such that, in the assembled electrode, the hydrogel is sandwiched between the carrier layer and a top layer. As a result of this configuration, both the adhesive underside of the carrier layer and a substantial portion of the hydrogel layer can contact the patient's skin, while the hydrogel itself cannot be detached from the electrode. This simple construction also reduces manufacturing costs, making the unit economical.

These and other objects, advantages, and features of the invention will be more fully understood and appreciated by reference to the written specification and appended drawings.

DESCRIPTION OF THE PREFERRED EMBODIMENT

Figure 1:
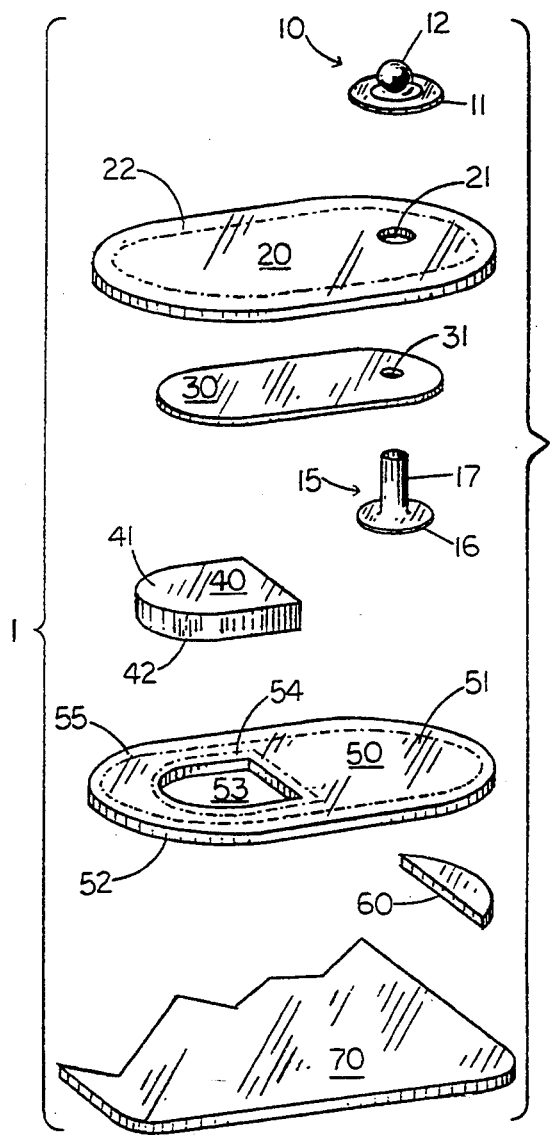
FIG. 1 is a perspective view of the disassembled elements of the electrode.
Figure 2:
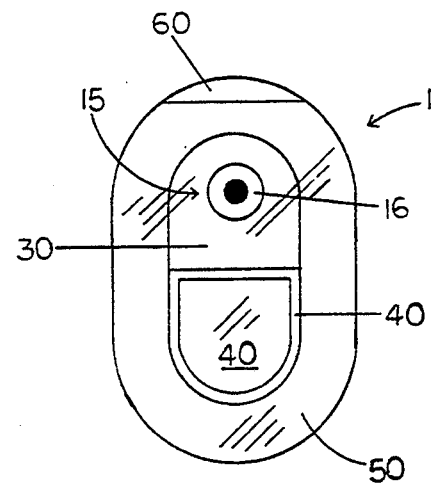
FIG. 2 shows a bottom plan view of the electrode.
Figure 3:
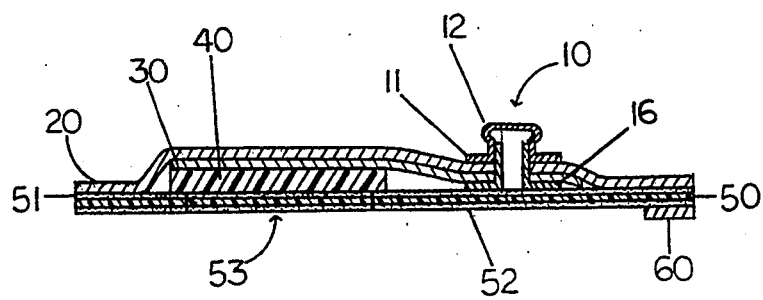
FIG. 3 illustrates a lateral cross-sectional view of the electrode, with the layers being somewhat enlarged for purposes of clarity.

In the preferred embodiment, a conductive stud 15, which serves as the electrical contact for the electrode, a spaced conductive hydrogel 40, and a conductive bridge layer 30 are sandwiched between a nonconductive, adhesive-coated carrier layer 50 and a nonconductive cover layer 20 (FIGS. 1 and 3). Both the conductive hydrogel 40 and the spaced, conductive stud 15 are connected by conductive bridge 30. Further, both conductive bridge 30 and overlying top layer 20 have aligned openings 21, 31 such that the post 17 of conductive stud 15 passes through both openings 21, 31 to be joined to conductive snap fastener 10, which rests on the cover layer 20 of the assembled electrode 1. An opening 53 in carrier layer 50 is of slightly smaller dimensions than hydrogel layer 40, such that the hydrogel 40 can contact a patient's skin without the risk of being detached frown the electrode 1. A release liner 70 is adhered to the exposed adhesive underside 52 of carrier layer 50 so as to cover the entire assembly, therebeing a small separation tab 60 adhered to the underside of carrier layer 50 near an edge thereof to facilitate subsequent peeling of release liner 70 away from adhesive undersurface 52 of carrier layer 50.

Any plastic material is suitable for use as carrier layer 50 of the present invention. However, it is preferable that the material of which the carrier layer 50 is made have sufficient tear strength such that the conductive stud 15 will not tear out of carrier layer 50 when the electrode is peeled away from the release liner 70.

An important aspect of the present invention is that carrier layer 50 have adhesive-coated top and bottom surfaces 51, 52. Adhesive surface 52 serves to adhere the electrode either to release liner 70 or, when in use, a patient's skin. Adhesive surface 51 adheres to portions of both hydrogel layer 40 and conductive bridge 30, as well as the base of conductive stud 15 and the periphery 22 of top layer 20. In this manner, the indicated conductive elements of the electrode are sandwiched in their desired positions between the adhesive surface 51 of carrier layer 50 and the underside of top layer 20.

Carrier layer 50 also includes an opening 53 of similar shape but slightly smaller dimensions than hydrogel layer 40. When the entire electrode is assembled according to the indicated sandwiching method, a portion of the undersurface 42 of hydrogel layer 40 is adhered to the adhesive surface 51 of carrier layer 50 at the indicated contact surfaces 54. Hydrogel layer 40 is thus permitted to contact a patient's skin through the opening 53 in carrier layer 50, while being prevented by a combination of the smaller size of opening 53 and the adhesive surface 51 of carrier layer 50 from being inadvertently or accidentally removed from the electrode.

Conductive stud 15 is of a conventional construction, preferably being made of stainless steel, nickel-plated brass, or the like to enhance conductivity. It comprises a generally circular stud base 16 from which projects a central stud post 17 which is narrower in diameter than stud base 16.

Likewise, snap fastener 10 is preferably of a conventional construction, being made of the same conductive stainless steel, nickel-plated brass, or like material. Snap fastener 10 is comprised of a generally circular base 11 and a hollow post 12 dimensioned such that stud post 17 will have a snug fit in snap fastener post 12 when the stud 15 and snap fastener 10 are forced together in the assembled electrode.

Hydrogel layer 40 is connected to the undersurface of conductive bridge 30 and the adhesive top layer 51 of the carrier layer 50 at top and bottom hydrogel surfaces 41 and 42, respectively. As indicated, hydrogel 40 is of slightly larger dimensions than the opening 53 in carrier layer 50, such that the perimeter of undersurface 42 of hydrogel 40 adheres to adhesive surface 51 of carrier layer 50 at contact surfaces 54. In the best mode contemplated for the present invention, this leaves a substantial portion of the undersurface 42 of hydrogel 40 to contact a patient's skin.

Hydrogel layer 40 can be comprised of any conductive gel material. However the preferred material is known in the art as hydrogel. Hydrogel is a polymeric material which is conductive, preferably hydrophilic, has low surface resistivity, and good adhesive properties. It is most preferably hypoallergenic and includes a bacteriostat and fungistat. Such materials are well-known to those skilled in the art.

Conductive bridge 30, which connects hydrogel layer 40 to the combination of conductive stud 15 and snap fastener 10, is preferably comprised of a metal matrix coated on the underside of a strip of polyester film. In the best mode contemplated for the present invention, this metal matrix is a silver-silver chloride ink, a coating process well-known in the art.

Conductive bridge 30 also includes an opening 31 at one end, aligned with the post 17 of conductive stud 15. In the assembled electrode, this opening 31 permits post 17 to pass through the conductive bridge 30. This configuration both permits post 17 to be ultimately joined with snap fastener 10 as well as allowing intimate electrical connection between the silver-silver chloride coating of conductive bridge 30 and the greater surface area of base 16 of stud 15.

Top layer 20 is preferably made of a thin piece of flexible paper, fabric, polymeric material or the like having substantially identical dimensions to the carrier layer 50. Unlike carrier layer 50, top layer 20 has no adhesive surfaces. Rather, the indicated conductive components of the electrode are generally centrally located and sandwiched between the carrier layer 50 and top layer 20 when the indicated perimeter 22 of top layer 20 is adhered to the corresponding perimeter area 55 of adhesive surface 51 of carrier layer 50.

As with conductive bridge 30, top layer 20 includes an opening 21 at one end, aligned with post 17 of stud 15. In the assembled electrode, post 17 also passes through opening 21, to be then joined with snap fastener 10.

Assembled medical electrodes 1 are individually or collectively mounted upon a release liner 70, which is preferably sufficiently stiff and rigid to be easily handled. Preferably, it is made of a thin sheet of relatively rigid plastic material, the adhesive-contacting surface of which resist bonding to the adhesive surface 52 of carrier layer 50, so that the electrode may be easily removed for use. A most preferred material is a silicone-coated polyester.

At one end of adhesive surface 52 of carrier layer 50 is attached a small separation tab 60, which permits the easy removal of the electrode from release liner 70. Preferably, separation tab 60 is made of a release-paper, the release liner abutting surface of which is coated with silicone or a similar adhesive-resistant compound.

Of course, it understood that the above is merely a preferred embodiment of the invention, and that various other embodiments as well as many changes and alterations, apparent to those skilled in the art, may be made without departing from the spirit and broader aspects of the invention as defined in the claims.

The embodiments of the invention in which an exclusive property or privilege is claimed are defined as follows:

1. A medical electrode comprising:
   a flexible carrier layer having an opening therethrough, and having upper and lower adhesively coated surfaces;
   a gel layer positioned over said opening and having horizontal dimensions larger than said opening whereby a marginal portion of said gel layer engages said upper surface of said carrier layer and is adhered thereto, said gel layer having horizontal dimensions smaller than said carrier layer whereby a marginal portion of said upper surface of said carrier layer remains exposed beyond the perimeter of said gel layer;

an electrical contact adhered to said adhesively coated upper surface of said carrier layer and electrically coupled to said gel layer;

a flexible top layer at least horizontally coextensive with said carrier layer and adhered to said marginal portion of said adhesively coated upper surface of said carrier layer whereby said marginal portion of said gel layer is trapped between said top layer and said carrier layer; and said top layer and said electrical contact being configured relative to one another such that a least a first portion of said electrical contact is trapped between said top layer and at least one of said carrier layer and said gel layer, and a second portion of said electrical contact is exposed whereby said electrical contact can be connected to a medical device.

2. The medical electrode of claim 1, wherein said electrical contact and said gel layer are laterally offset from one another, and are electrically coupled by a conductive bridge extending from said gel layer to said contact, said bridge adhered to said adhesively coated upper surface of said carrier layer, said conductive bridge smaller in horizontal dimensions than said carrier and top layers, and said carrier and top layers being adhered together beyond the perimeter of said conductive bridge.

3. The medical electrode of claim 2, in which said electrical contact comprises a base with a stem projecting therefrom, said base extending laterally beyond the lateral dimensions of said stem such that a portion of said base comprising said first portion of said contact, and said stem projecting upwardly through an opening in said top layer and comprising said second portion of said contact.

4. The medical electrode of claim 3, wherein the combination of said gel layer, said spaced electrical contact and said conductive bridge are attached to a central region of said carrier layer, such that the entire perimeter of said carrier layer is unoccupied and available to be attached to the corresponding perimeter of said top layer.

5. The medical electrode of claim 4, in which said carrier layer is of a flexible polymeric material of sufficient strength to avoid being torn by said electrical contact when said electrode is bent or flexed.

6. The electrode of claim 5, in which said gel layer comprises a layer of hydrogel material.

7. The electrode of claim 6, wherein said conductive bridge comprises a strip of polyester film with at least a lower surface contacting said gel layer, and coated with a conductive material.

8. The medical electrode of claim 7, in which at least a portion of said base of said electrical contact is located below said lower surface of said conductive bridge whereby electrical contact between said contact and said conductive bridge is effected.

9. The medical electrode of claim 8, wherein said conductive material coating comprises a silver-silver chloride ink.

10. The medical electrode of claim 9, in which said top layer comprises a fabric layer of sufficient strength to avoid tearing when the electrode is flexed, bent, or generally handled.

11. The electrode of claim 4, wherein said conductive bridge comprises a strip of polyester film with at least a lower surface coated with a conductive material.

12. The medical electrode of claim 11, in which at least a portion of said base of said electrical contact is located below said lower surface of said conductive bridge whereby electrical contact between said contact and said conductive bridge is effected.

13. The medical electrode of claim 2, wherein the combination of said gel layer, said spaced electrical contact and said conductive bridge are attached to a central region of said carrier layer, such that the entire perimeter of said carrier layer is unoccupied and available to be attached to the corresponding perimeter of said top layer.

14. The medical electrode of claim 1, in which said electrical contact and said gel layer are laterally offset from one another, and are electrically coupled by a conductive bridge extending from said gel layer to said contact, said bridge being located between said top layer and said carrier layer and being smaller in horizontal dimensions than said carrier and top layers, said carrier and top layers being adhered together beyond the perimeter of said bridge.

15. The medical electrode of claim 14, in which said electrical contact comprises a base with a stem projecting therefrom, said base extending laterally beyond the lateral dimensions of said stem such that a portion of said base comprising said first portion of said contact, and said stem projecting upwardly through an opening in said top layer and comprising said second portion of said contact.

16. The medical electrode of claim 1, in which said electrical contact comprises a base with a stem projecting therefrom, said base extending laterally beyond the lateral dimensions of said stem such that a portion of said base comprising said first portion of said contact, and said stem projecting upwardly through an opening in said top layer and comprising said second portion of said contact.

17. The medical electrode of claim 1, in which said carrier layer is of a flexible polymeric material of sufficient strength to avoid being torn by said electrical contact when said electrode is bent or flexed.

18. The electrode of claim 17, wherein said conductive bridge comprises a strip of polyester film with at least a lower surface contacting said gel layer, being coated with a conductive material.

19. The electrode of claim 1, in which said gel layer comprises a layer of hydrogel material.

20. A medical electrode comprising:

a carrier layer having an adhesively coated upper surface, and adhesively coated lower surface for adherence to a patient when said electrode is in use, and an opening therethrough;

a conductive gel layer at least coextensive with said opening, including a portion smaller in horizontal dimensions than said upper surface of said carrier layer and adhered thereto, whereby a marginal portion of said adhesively coated upper surface of said carrier layer beyond the perimeter of said gel layer remains exposed;

an electrical contact offset from said gel layer and in contact with and adhered to said exposed marginal portion of said adhesively coated upper surface of said carrier layer;

a top layer at least horizontally coextensive with said carrier layer and being in contact with and thereby adhered to said marginal portion of said carrier layer;

a conductive bridge interconnecting said gel layer and said electrical contact and adhered to said adhesively coated upper surface of said carrier layer, said conductive bridge smaller in horizontal dimensions than said carrier and top layers, said carrier and top layers being adhered together beyond the perimeter of said bridge; and said top layer and said electrical contact being configured relative to one another such that at least a first portion of said electrical contact is trapped between said top layer and said carrier layer, and a second portion of said electrical contact is exposed whereby said electrical contact can be connected to a medical device.

21. The medical electrode of claim 20, in which said conductive bridge extends between said first portion of said contact and said top layer.

22. The medical electrode of claim 21, in which said electrical contact comprises a base with a stem projecting therefrom, said base extending laterally beyond the lateral dimensions of said stem such that a portion of said base comprising said first portion of said contact, and said stem projecting upwardly through an opening in said top layer and comprising said second portion of said contact.

23. The electrode of claim 22, wherein said conductive bridge comprises a strip of polyester film with a lower surface coated with a conductive material.

24. The medical electrode of claim 20, in which said electrical contact comprises a base with a stem projecting therefrom, said base extending laterally beyond the lateral dimensions of said stem such that a portion of said base comprising said first portion of said contact, and said stem projecting upwardly through an opening in said top layer and comprising said second portion of said contact.

25. A method for constructing a medical electrode comprising:

providing a carrier layer having an adhesively coated upper surface, an adhesively coated lower surface and an opening therethrough;

adhering a gel layer to a portion of said upper surface of said carrier layer, overlying said opening therethrough, but leaving a marginal portion of said adhesively coated upper surface of said carrier exposed beyond the perimeter of said gel layer;

electrically coupling an electrical contact to said gel layer;

applying a top layer over at least a first portion of said electrical contact, said gel layer and said carrier layer and adhering said top layer to said adhesively coated exposed marginal portion of said carrier layer upper surface; and configuring said top layer relative to said electrical contact such that a second portion of said electrical contact is exposed to facilitate connection with a medical device.

26. The method of claim 25, which includes offsetting said electrical contact from said gel layer and adhering said electrical contact to said adhesively coated upper surface of said carrier layer; and placing a conductive bridge over said gel layer and over at least said first portion of said electrical contact, and below said top layer, said bridge smaller in horizontal dimensions than said carrier and top layers such that said bridge is adhered to said upper surface of said carrier layer, and said carrier and top layers are adhered together beyond the perimeter of said bridge.

27. The method of claim 26, wherein electrically coupling said electrical contact to said gel layer, includes providing a base with a stem projecting therefrom, said base adhered to said upper surface of said carrier layer and extending laterally beyond the lateral dimensions of said stem, and projecting said stem upwardly through an opening in said bridge and top layer to define said second portion of said electrical contact.

28. The method of claim 27, further including attaching said gel layer, said spaced electrical contact and said conductive bridge to a central region of said carrier layer, such that the entire perimeter of said carrier layer is unoccupied and available to be attached to the corresponding perimeter of said top layer.

* * * * *